United States Patent
Kestelli et al.

(10) Patent No.: US 10,285,626 B1
(45) Date of Patent: May 14, 2019

(54) ACTIVITY IDENTIFICATION USING AN OPTICAL HEART RATE MONITOR

(71) Applicant: Apple Inc., Cupertino, CA (US)

(72) Inventors: Nevzat Akin Kestelli, Cupertino, CA (US); Ueyn L. Block, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 14/569,346

(22) Filed: Dec. 12, 2014

Related U.S. Application Data

(60) Provisional application No. 61/940,364, filed on Feb. 14, 2014.

(51) Int. Cl.
| | |
|---|---|
| *A61B 5/11* | (2006.01) |
| *A61B 5/0205* | (2006.01) |
| *A61B 5/00* | (2006.01) |
| *A61B 5/024* | (2006.01) |

(52) U.S. Cl.
CPC .......... *A61B 5/1118* (2013.01); *A61B 5/0205* (2013.01); *A61B 5/6802* (2013.01); *A61B 5/7207* (2013.01); *A61B 5/7282* (2013.01); *A61B 5/742* (2013.01); *A61B 5/02416* (2013.01)

(58) Field of Classification Search
None
See application file for complete search history.

(56) References Cited

U.S. PATENT DOCUMENTS

| | | | |
|---|---|---|---|
| 4,686,572 A | 8/1987 | Takatsu | |
| 4,686,648 A | 8/1987 | Fossum | |
| 5,105,264 A | 4/1992 | Erhardt et al. | |
| 5,329,313 A | 7/1994 | Keith | |
| 5,396,893 A | 3/1995 | Oberg et al. | |
| 5,471,515 A | 11/1995 | Fossum et al. | |
| 5,541,402 A | 7/1996 | Ackland | |
| 5,550,677 A | 8/1996 | Schofield et al. | |

(Continued)

FOREIGN PATENT DOCUMENTS

| | | |
|---|---|---|
| CN | 1630350 | 6/2005 |
| CN | 1774032 | 5/2006 |

(Continued)

OTHER PUBLICATIONS

Aoki, et al., "Rolling-Shutter Distortion-Free 3D Stacked Image Sensor with −160dB Parasitic Light Sensitivity In-Pixel Storage Node," ISSCC 2013, Session 27, Image Sensors, 27.3 27.3 A, Feb. 20, 2013, retrieved on Apr. 11, 2014 from URL:http://ieeexplore.ieee.org/stamp/stamp.jsp?tp=&arnumber=6487824.

(Continued)

*Primary Examiner* — Niketa I Patel
*Assistant Examiner* — Nathan A Baldwin
(74) *Attorney, Agent, or Firm* — Brownstein Hyatt Farber Schreck, LLP

(57) ABSTRACT

An electronic device that can be worn by a user can include a processing device and one or more optical heart rate monitors operatively connected to the processing device. The processing device can be adapted to receive a OHRM signal from at least one optical heart rate monitor. The OHRM signal includes one or more motion artifacts that are produced by a physical activity of the user. The processing device can be adapted to analyze the OHRM signal to determine the physical activity of the user.

18 Claims, 6 Drawing Sheets

(56) References Cited

U.S. PATENT DOCUMENTS

| | | |
|---|---|---|
| 5,781,312 A | 7/1998 | Noda |
| 5,841,126 A | 11/1998 | Fossum et al. |
| 5,880,459 A | 3/1999 | Pryor et al. |
| 5,949,483 A | 9/1999 | Fossum et al. |
| 6,008,486 A | 12/1999 | Stam et al. |
| 6,040,568 A | 3/2000 | Caulfield et al. |
| 6,233,013 B1 | 5/2001 | Hosier et al. |
| 6,348,929 B1 | 2/2002 | Acharya et al. |
| 6,448,550 B1 | 9/2002 | Nishimura |
| 6,528,833 B2 | 3/2003 | Lee et al. |
| 6,541,751 B1 | 4/2003 | Bidermann |
| 6,670,904 B1 | 12/2003 | Yakovlev |
| 6,713,796 B1 | 3/2004 | Fox |
| 6,714,239 B2 | 3/2004 | Guidash |
| 6,798,453 B1 | 9/2004 | Kaifu |
| 6,816,676 B2 | 11/2004 | Bianchi et al. |
| 6,905,470 B2 | 6/2005 | Lee et al. |
| 6,956,605 B1 | 10/2005 | Hashimoto |
| 6,982,759 B2 | 1/2006 | Goto |
| 7,075,049 B2 | 7/2006 | Rhodes et al. |
| 7,091,466 B2 | 8/2006 | Bock |
| 7,119,322 B2 | 10/2006 | Hong |
| 7,133,073 B1 | 11/2006 | Neter |
| 7,259,413 B2 | 8/2007 | Rhodes |
| 7,262,401 B2 | 8/2007 | Hopper et al. |
| 7,271,835 B2 | 9/2007 | Iizuka et al. |
| 7,282,028 B2 | 10/2007 | Kim et al. |
| 7,319,218 B2 | 1/2008 | Krymski |
| 7,332,786 B2 | 2/2008 | Altice |
| 7,390,687 B2 | 6/2008 | Boettiger |
| 7,415,096 B2 | 8/2008 | Sherman |
| 7,437,013 B2 | 10/2008 | Anderson |
| 7,443,421 B2 | 10/2008 | Stavely et al. |
| 7,446,812 B2 | 11/2008 | Ando et al. |
| 7,471,315 B2 | 12/2008 | Silsby et al. |
| 7,502,054 B2 | 3/2009 | Kalapathy |
| 7,525,168 B2 | 4/2009 | Hsieh |
| 7,554,067 B2 | 6/2009 | Zarnoski et al. |
| 7,555,158 B2 | 6/2009 | Park et al. |
| 7,589,316 B2 | 9/2009 | Dunki-Jacobs |
| 7,626,626 B2 | 10/2009 | Panicacci |
| 7,622,699 B2 | 11/2009 | Sakakibara et al. |
| 7,636,109 B2 | 12/2009 | Nakajima et al. |
| 7,667,400 B1 | 2/2010 | Goushcha |
| 7,671,435 B2 | 3/2010 | Ahn |
| 7,714,292 B2 | 5/2010 | Agarwal et al. |
| 7,728,351 B2 | 6/2010 | Shim |
| 7,733,402 B2 | 6/2010 | Egawa et al. |
| 7,742,090 B2 | 6/2010 | Street |
| 7,764,312 B2 | 7/2010 | Ono et al. |
| 7,773,138 B2 | 8/2010 | Lahav et al. |
| 7,786,543 B2 | 8/2010 | Hsieh |
| 7,796,171 B2 | 9/2010 | Gardner |
| 7,817,198 B2 | 10/2010 | Kang et al. |
| 7,838,956 B2 | 11/2010 | McCarten et al. |
| 7,873,236 B2 | 1/2011 | Li et al. |
| 7,880,785 B2 | 2/2011 | Gallagher |
| 7,884,402 B2 | 2/2011 | Ki |
| 7,906,826 B2 | 3/2011 | Martin et al. |
| 7,952,121 B2 | 5/2011 | Arimoto |
| 7,952,635 B2 | 5/2011 | Lauxtermann |
| 7,982,789 B2 | 7/2011 | Watanabe et al. |
| 8,026,966 B2 | 9/2011 | Altice |
| 8,032,206 B1 | 10/2011 | Farazi et al. |
| 8,089,036 B2 | 1/2012 | Manabe et al. |
| 8,089,524 B2 | 1/2012 | Urisaka |
| 8,094,232 B2 | 1/2012 | Kusaka |
| 8,116,540 B2 | 2/2012 | Dean |
| 8,140,143 B2 | 3/2012 | Picard et al. |
| 8,153,947 B2 | 4/2012 | Barbier et al. |
| 8,159,570 B2 | 4/2012 | Negishi |
| 8,159,588 B2 | 4/2012 | Boemler |
| 8,164,669 B2 | 4/2012 | Compton et al. |
| 8,174,595 B2 | 5/2012 | Honda et al. |
| 8,184,188 B2 | 5/2012 | Yaghmai |
| 8,194,148 B2 | 6/2012 | Doida |
| 8,194,165 B2 | 6/2012 | Border et al. |
| 8,222,586 B2 | 7/2012 | Lee |
| 8,227,844 B2 | 7/2012 | Adkisson et al. |
| 8,233,071 B2 | 7/2012 | Takeda |
| 8,259,228 B2 | 9/2012 | Wei et al. |
| 8,310,577 B1 | 11/2012 | Neter |
| 8,324,553 B2 | 12/2012 | Lee |
| 8,338,856 B2 | 12/2012 | Tai et al. |
| 8,340,407 B2 | 12/2012 | Kalman |
| 8,350,940 B2 | 1/2013 | Smith et al. |
| 8,355,117 B2 | 1/2013 | Niclass |
| 8,388,346 B2 | 3/2013 | Rantala et al. |
| 8,400,546 B2 | 3/2013 | Itano et al. |
| 8,456,540 B2 | 6/2013 | Egawa |
| 8,456,559 B2 | 6/2013 | Yamashita |
| 8,508,637 B2 | 8/2013 | Han et al. |
| 8,514,308 B2 | 8/2013 | Itonaga et al. |
| 8,520,913 B2 | 8/2013 | Dean |
| 8,546,737 B2 | 10/2013 | Tian et al. |
| 8,547,388 B2 | 10/2013 | Cheng |
| 8,575,531 B2 | 11/2013 | Hynecek et al. |
| 8,581,992 B2 | 11/2013 | Hamada |
| 8,594,170 B2 | 11/2013 | Mombers et al. |
| 8,619,163 B2 | 12/2013 | Ogua |
| 8,619,170 B2 | 12/2013 | Mabuchi |
| 8,629,484 B2 | 1/2014 | Ohri et al. |
| 8,634,002 B2 | 1/2014 | Kita |
| 8,637,875 B2 | 1/2014 | Finkelstein et al. |
| 8,648,947 B2 | 2/2014 | Sato et al. |
| 8,653,434 B2 | 2/2014 | Johnson et al. |
| 8,723,975 B2 | 5/2014 | Solhusvik |
| 8,724,096 B2 | 5/2014 | Gosch et al. |
| 8,730,345 B2 | 5/2014 | Watanabe |
| 8,754,983 B2 | 6/2014 | Sutton |
| 8,755,854 B2 | 6/2014 | Addison et al. |
| 8,759,736 B2 | 6/2014 | Yoo |
| 8,760,413 B2 | 6/2014 | Peterson et al. |
| 8,767,104 B2 | 7/2014 | Makino et al. |
| 8,803,990 B2 | 8/2014 | Smith |
| 8,817,154 B2 | 8/2014 | Manabe et al. |
| 8,879,686 B2 | 11/2014 | Okada et al. |
| 8,902,330 B2 | 12/2014 | Theuwissen |
| 8,908,073 B2 | 12/2014 | Minagawa |
| 8,934,030 B2 | 1/2015 | Kim et al. |
| 8,946,610 B2 | 2/2015 | Iwabuchi et al. |
| 8,982,237 B2 | 3/2015 | Chen |
| 9,041,837 B2 | 5/2015 | Li |
| 9,017,748 B2 | 6/2015 | Theuwissen |
| 9,054,009 B2 | 6/2015 | Oike et al. |
| 9,058,081 B2 | 6/2015 | Baxter |
| 9,066,017 B2 | 6/2015 | Geiss |
| 9,066,660 B2 | 6/2015 | Watson et al. |
| 9,088,727 B2 | 7/2015 | Trumbo |
| 9,094,623 B2 | 7/2015 | Kawaguchi |
| 9,099,604 B2 | 8/2015 | Roy |
| 9,100,597 B2 | 8/2015 | Hu |
| 9,106,859 B2 | 8/2015 | Kizuna et al. |
| 9,131,171 B2 | 9/2015 | Aoki et al. |
| 9,160,949 B2 | 10/2015 | Zhang et al. |
| 9,164,144 B2 | 10/2015 | Dolinsky |
| 9,178,100 B2 | 11/2015 | Webster et al. |
| 9,209,320 B1 | 12/2015 | Webster |
| 9,232,150 B2 | 1/2016 | Kleekajai et al. |
| 9,232,161 B2 | 1/2016 | Suh |
| 9,235,267 B2 | 1/2016 | Burrough et al. |
| 9,270,906 B2 | 2/2016 | Peng et al. |
| 9,287,304 B2 | 3/2016 | Park et al. |
| 9,288,380 B2 | 3/2016 | Nomura |
| 9,331,116 B2 | 5/2016 | Webster |
| 9,344,649 B2 | 5/2016 | Bock |
| 9,417,326 B2 | 8/2016 | Niclass et al. |
| 9,438,258 B1 | 9/2016 | Yoo |
| 9,445,018 B2 | 9/2016 | Fettig et al. |
| 9,448,110 B2 | 9/2016 | Wong |
| 9,478,030 B1 | 10/2016 | Lecky |
| 9,497,397 B1 | 11/2016 | Kleekajai et al. |
| 9,516,244 B2 | 12/2016 | Borowski |
| 9,560,339 B2 | 1/2017 | Borowski |

(56) References Cited

U.S. PATENT DOCUMENTS

| | | |
|---|---|---|
| 9,584,743 B1 | 2/2017 | Lin et al. |
| 9,596,423 B1 | 3/2017 | Molgaard |
| 9,749,556 B2 | 8/2017 | Fettig et al. |
| 9,774,318 B2 | 9/2017 | Song |
| 9,781,368 B2 | 10/2017 | Song |
| 9,831,283 B2 | 11/2017 | Shepard et al. |
| 9,888,198 B2 | 2/2018 | Mauritzson et al. |
| 9,894,304 B1 | 2/2018 | Smith |
| 9,912,883 B1 | 3/2018 | Agranov et al. |
| 10,136,090 B2 | 11/2018 | Vogelsang et al. |
| 10,153,310 B2 | 12/2018 | Zhang et al. |
| 2003/0036685 A1 | 2/2003 | Goodman et al. |
| 2004/0207836 A1 | 10/2004 | Chhibber et al. |
| 2005/0026332 A1 | 2/2005 | Fratti et al. |
| 2005/0049470 A1* | 3/2005 | Terry ............. A61B 5/14552 600/323 |
| 2006/0274161 A1 | 12/2006 | Ing et al. |
| 2007/0263099 A1 | 11/2007 | Motta et al. |
| 2008/0177162 A1 | 7/2008 | Bae et al. |
| 2008/0315198 A1 | 12/2008 | Jung |
| 2009/0096901 A1 | 4/2009 | Bae et al. |
| 2009/0101914 A1 | 4/2009 | Hirotsu et al. |
| 2009/0146234 A1 | 6/2009 | Luo et al. |
| 2009/0201400 A1 | 8/2009 | Zhang et al. |
| 2009/0219266 A1 | 9/2009 | Lim et al. |
| 2010/0134631 A1 | 6/2010 | Voth |
| 2011/0080500 A1 | 4/2011 | Wang et al. |
| 2011/0152637 A1* | 6/2011 | Kateraas ............. A61B 5/02055 600/301 |
| 2011/0156197 A1 | 6/2011 | Tivarus et al. |
| 2011/0164162 A1 | 7/2011 | Kato |
| 2011/0193824 A1 | 8/2011 | Modarres et al. |
| 2011/0245690 A1 | 10/2011 | Watson et al. |
| 2012/0092541 A1 | 4/2012 | Tuulos et al. |
| 2012/0098964 A1 | 4/2012 | Oggier et al. |
| 2012/0127088 A1 | 5/2012 | Pance et al. |
| 2012/0147207 A1 | 6/2012 | Itonaga |
| 2012/0239173 A1* | 9/2012 | Laikari ............. A61B 5/1112 700/91 |
| 2013/0147981 A1 | 6/2013 | Wu |
| 2013/0155271 A1 | 6/2013 | Ishii |
| 2013/0222584 A1 | 8/2013 | Aoki et al. |
| 2014/0049683 A1 | 2/2014 | Guenter |
| 2014/0071321 A1 | 3/2014 | Seyama |
| 2014/0132528 A1 | 5/2014 | Catton |
| 2014/0167973 A1* | 6/2014 | Letchner ............. A61B 5/1118 340/870.02 |
| 2014/0231630 A1 | 8/2014 | Rae et al. |
| 2014/0240550 A1 | 8/2014 | Taniguchi |
| 2014/0246568 A1 | 9/2014 | Wan |
| 2014/0247378 A1 | 9/2014 | Sharma et al. |
| 2014/0252201 A1 | 9/2014 | Li et al. |
| 2014/0253754 A1 | 9/2014 | Papiashvili |
| 2014/0263951 A1 | 9/2014 | Fan et al. |
| 2014/0267855 A1 | 9/2014 | Fan |
| 2014/0347533 A1 | 11/2014 | Toyoda |
| 2014/0354861 A1 | 12/2014 | Pang |
| 2015/0062391 A1 | 3/2015 | Murata |
| 2015/0163392 A1 | 6/2015 | Malone et al. |
| 2015/0163422 A1 | 6/2015 | Fan et al. |
| 2015/0215443 A1* | 7/2015 | Heo ............. H04M 1/0202 455/556.1 |
| 2015/0237314 A1 | 8/2015 | Hasegawa |
| 2015/0264241 A1 | 9/2015 | Kleekajai et al. |
| 2015/0264278 A1 | 9/2015 | Kleekajai et al. |
| 2015/0277559 A1 | 10/2015 | Vescovi et al. |
| 2015/0312479 A1 | 10/2015 | McMahon et al. |
| 2015/0350575 A1 | 12/2015 | Agranov et al. |
| 2016/0050379 A1 | 2/2016 | Jiang et al. |
| 2016/0099371 A1 | 4/2016 | Webster |
| 2016/0205311 A1 | 7/2016 | Mandelli et al. |
| 2016/0218236 A1 | 7/2016 | Dhulla et al. |
| 2016/0219232 A1 | 7/2016 | Murata |
| 2016/0274237 A1 | 9/2016 | Stutz |
| 2016/0307325 A1 | 10/2016 | Wang et al. |
| 2016/0356890 A1 | 12/2016 | Fried et al. |
| 2016/0365380 A1 | 12/2016 | Wan |
| 2017/0047363 A1 | 2/2017 | Choi et al. |
| 2017/0082746 A1 | 3/2017 | Kubota et al. |
| 2017/0084133 A1 | 3/2017 | Cardinali et al. |
| 2017/0142325 A1 | 5/2017 | Shimokawa et al. |
| 2017/0223292 A1 | 8/2017 | Ikeda |
| 2017/0272675 A1 | 9/2017 | Kobayashi |
| 2017/0373106 A1 | 12/2017 | Li et al. |
| 2018/0213205 A1 | 7/2018 | Oh |

FOREIGN PATENT DOCUMENTS

| | | |
|---|---|---|
| CN | 1833429 | 9/2006 |
| CN | 1842138 | 10/2006 |
| CN | 1947414 | 4/2007 |
| CN | 101189885 | 5/2008 |
| CN | 101221965 | 7/2008 |
| CN | 101233763 | 7/2008 |
| CN | 101472059 | 7/2009 |
| CN | 101567977 | 10/2009 |
| CN | 101622859 | 1/2010 |
| CN | 101739955 | 6/2010 |
| CN | 101754029 | 6/2010 |
| CN | 101803925 | 8/2010 |
| CN | 102036020 | 4/2011 |
| CN | 102067584 | 5/2011 |
| CN | 102208423 | 10/2011 |
| CN | 102451160 | 5/2012 |
| CN | 102668542 | 9/2012 |
| CN | 102820309 | 12/2012 |
| CN | 102821255 | 12/2012 |
| CN | 103024297 | 4/2013 |
| CN | 103051843 | 4/2013 |
| CN | 103329513 | 9/2013 |
| CN | 103546702 | 1/2014 |
| CN | 204761615 | 11/2015 |
| EP | 1763228 | 3/2007 |
| EP | 2023611 | 2/2009 |
| EP | 2107610 | 10/2009 |
| EP | 2230690 | 9/2010 |
| EP | 2512126 | 10/2012 |
| EP | 2787531 | 10/2014 |
| JP | S61123287 | 6/1986 |
| JP | 2007504670 | 8/1987 |
| JP | 2000059697 | 2/2000 |
| JP | 2001211455 | 8/2001 |
| JP | 2001358994 | 12/2001 |
| JP | 2004111590 | 4/2004 |
| JP | 2005318504 | 11/2005 |
| JP | 2006287361 | 10/2006 |
| JP | 2007516654 | 6/2007 |
| JP | 2008507908 | 3/2008 |
| JP | 2008271280 | 11/2008 |
| JP | 2008543061 | 11/2008 |
| JP | 2009021809 | 1/2009 |
| JP | 2009159186 | 7/2009 |
| JP | 2009212909 | 9/2009 |
| JP | 2009296465 | 12/2009 |
| JP | 2010080604 | 4/2010 |
| JP | 2010114834 | 5/2010 |
| JP | 2011040926 | 2/2011 |
| JP | 201149697 | 3/2011 |
| JP | 2011091775 | 5/2011 |
| JP | 2011097646 | 12/2011 |
| JP | 2012010306 | 1/2012 |
| JP | 2012019516 | 1/2012 |
| JP | 2012513160 | 6/2012 |
| JP | 2013051523 | 3/2013 |
| JP | 2013070240 | 4/2013 |
| JP | 2013529035 | 7/2013 |
| KR | 20030034424 | 5/2003 |
| KR | 20030061157 | 7/2003 |
| KR | 20050103732 | 11/2005 |
| KR | 2008/0069851 | 7/2008 |
| KR | 20100008239 | 1/2010 |
| KR | 20100065084 | 6/2010 |
| KR | 20130074459 | 7/2013 |

(56) References Cited

FOREIGN PATENT DOCUMENTS

| | | |
|---|---|---|
| TW | 200520551 | 6/2005 |
| TW | 200803481 | 1/2008 |
| TW | 201110689 | 3/2011 |
| TW | 201301881 | 1/2013 |
| WO | WO 05/041304 | 5/2005 |
| WO | WO 06/014641 | 2/2006 |
| WO | WO 06/130443 | 12/2006 |
| WO | WO 07/049900 | 5/2007 |
| WO | WO 10/120945 | 10/2010 |
| WO | WO 12/011095 | 1/2012 |
| WO | WO 12/032353 | 3/2012 |
| WO | WO 12/053363 | 4/2012 |
| WO | WO 12/088338 | 6/2012 |
| WO | WO 12/122572 | 9/2012 |
| WO | WO 12/138687 | 10/2012 |
| WO | WO 13/008425 | 1/2013 |
| WO | WO 13/179018 | 12/2013 |
| WO | WO 13/179020 | 12/2013 |

OTHER PUBLICATIONS

Elgendi, "On the Analysis of Fingertip Photoplethysmogram Signals," *Current Cardiology Reviews*, 2012, vol. 8, pp. 14-25.
Feng, et al., "On the Stoney Formula for a Thin Film/Substrate System with Nonuniform Substrate Thickness," *Journal of Applied Mechanics*, Transactions of the ASME, vol. 74, Nov. 2007, pp. 1276-1281.
Fu, et al., "Heart Rate Extraction from Photoplethysmogram Waveform Using Wavelet Multui-resolution Analysis," *Journal of Medical and Biological Engineering*, 2008, vol. 28, No. 4, pp. 229-232.
Han, et al., "Artifacts in wearable photoplethysmographs during daily life motions and their reduction with least mean square based active noise cancellation method," *Computers in Biology and Medicine*, 2012, vol. 42, pp. 387-393.
Lopez-Silva, et al., "Heuristic Algorithm for Photoplethysmographic Heart Rate Tracking During Maximal Exercise Test," *Journal of Medical and Biological Engineering*, 2011, vol. 12, No. 3, pp. 181-188.
Santos, et al., "Accelerometer-assisted PPG Measurement During Physical Exercise Using the LAVIMO Sensor System," *Acta Polytechnica*, 2012, vol. 52, No. 5, pp. 80-85.
Sarkar, et al., "Fingertip Pulse Wave (PPG signal) Analysis and Heart Rate Detection," *International Journal of Emerging Technology and Advanced Engineering*, 2012, vol. 2, No. 9, pp. 404-407.
Schwarzer, et al., On the determination of film stress from substrate bending: Stoney's formula and its limits, Jan. 2006, 19 pages.
Yan, et al., "Reduction of motion artifact in pulse oximetry by smoothed pseudo Wigner-Ville distribution," *Journal of NeuroEngineering and Rehabilitation*, 2005, vol. 2, No. 3, pp. 1-9.
Yousefi, et al., "Adaptive Cancellation of Motion Artifact in Wearable Biosensors," 34th Annual International Conference of the IEEE EMBS, San Diego, California, Aug./Sep. 2012, pp. 2004-2008.
U.S. Appl. No. 15/056,752, filed Feb. 29, 2016, Wan.
U.S. Appl. No. 15/590,775, filed May 9, 2017, Lee.
Shen et al., "Stresses, Curvatures, and Shape Changes Arising from Patterned Lines on Silicon Wafers," Journal of Applied Physics, vol. 80, No. 3, Aug. 1996, pp. 1388-1398.
U.S. Appl. No. 15/627,409, filed Jun. 19, 2017, Agranov et al.
U.S. Appl. No. 15/653,458, filed Jul. 18, 2017, Zhang et al.
U.S. Appl. No. 15/682,255, filed Aug. 21, 2017, Li et al.
U.S. Appl. No. 15/699,806, filed Sep. 8, 2017, Li et al.
U.S. Appl. No. 15/713,477, filed Sep. 22, 2017, Mandai et al.
U.S. Appl. No. 15/713,520, filed Sep. 22, 2017, Mandai et al.
Charbon, et al., SPAD-Based Sensors, *TOF Range-Imaging Cameras*, F. Remondino and D. Stoppa (eds.), 2013, Springer-Verlag Berlin Heidelberg, pp. 11-38.
Cox, "Getting histograms with varying bin widths," http://www.stata.com/support/faqs/graphics/histograms-with-varying-bin-widths/, Nov. 13, 2017, 5 pages.
Gallivanoni, et al., "Progress n Quenching Circuits for Single Photon Avalanche Diodes," IEEE Transactions on Nuclear Science, vol. 57, No. 6, Dec. 2010, pp. 3815-3826.
Leslar, et al., "Comprehensive Utilization of Temporal and Spatial Domain Outlier Detection Methods for Mobile Terrestrial LiDAR Data," Remote Sensing, 2011, vol. 3, pp. 1724-1742.
Mota, et al., "A flexible multi-channel high-resolution Time-to-Digital Converter ASIC," *Nuclear Science Symposium Conference Record IEEE*, 2000, Engineering School of Geneva, Microelectronics Lab, Geneva, Switzerland, 8 pages.
Niclass, et al., "Design and Characterization of a CMOS 3-D Image Sensor Based on Single Photon Avalanche Diodes," *IEEE Journal of Solid-State Circuits*, vol. 40, No. 9, Sep. 2005, pp. 1847-1854.
Shin, et al., "Photon-Efficient Computational 3D and Reflectivity Imaging with Single-Photon Detectors," IEEE International Conference on Image Processing, Paris, France, Oct. 2014, 11 pages.
Tisa, et al., "Variable-Load Quenching Circuit for single-photon avalanche diodes," Optics Express, vol. 16, No. 3, Feb. 4, 2008, pp. 2232-2244.
Ullrich, et al., "Linear LIDAR versus Geiger-mode LIDAR: Impact on data properties and data quality," *Laser Radar Technology and Applications XXI*, edited by Monte D. Turner, Gary W. Kamerman, Proc. of SPIE, vol. 9832, 983204, 2016, 17 pages.
U.S. Appl. No. 15/879,365, filed Jan. 24, 2018, Mandai et al.
U.S. Appl. No. 15/879,350, filed Jan. 24, 2018, Mandai et al.
U.S. Appl. No. 15/880,285, filed Jan. 25, 2018, Laifenfeld et al.
U.S. Appl. No. 13/782,532, filed Mar. 1, 2013, Sharma et al.
U.S. Appl. No. 13/783,536, filed Mar. 4, 2013, Wan.
U.S. Appl. No. 13/785,070, filed Mar. 5, 2013, Li.
U.S. Appl. No. 13/787,094, filed Mar. 6, 2013, Li et al.
U.S. Appl. No. 13/797,851, filed Mar. 12, 2013, Li.
U.S. Appl. No. 13/830,748, filed Mar. 14, 2013, Fan.
U.S. Appl. No. 14/098,504, filed Dec. 5, 2013, Fan et al.
U.S. Appl. No. 14/207,150, filed Mar. 12, 2014, Kleekajai et al.
U.S. Appl. No. 14/207,176, filed Mar. 12, 2014, Kleekajai et al.
U.S. Appl. No. 14/276,728, filed May 13, 2014, McMahon et al.
U.S. Appl. No. 14/292,599, filed May 30, 2014, Agranov et al.
U.S. Appl. No. 14/462,032, filed Aug. 18, 2014, Jiang et al.
U.S. Appl. No. 14/481,806, filed Sep. 9, 2014, Kleekajai et al.
U.S. Appl. No. 14/481,820, filed Sep. 9, 2014, Lin et al.
U.S. Appl. No. 14/501,429, filed Sep. 30, 2014, Malone et al.
U.S. Appl. No. 14/503,322, filed Sep. 30, 2014, Molgaard.
U.S. Appl. No. 14/611,917, filed Feb. 2, 2015, Lee et al.
Jahromi et al., "A Single Chip Laser Radar Receiver with a 9x9 SPAD Detector Array and a 10-channel TDC," 2013 Proceedings of the ESSCIRC, IEEE, Sep. 14, 2015, pp. 364-367.

\* cited by examiner

ACTIVITY IDENTIFICATION USING AN OPTICAL HEART RATE MONITOR

CROSS-REFERENCE TO RELATED APPLICATION

This application claims the benefit under 35 U.S.C. § 119(e) of U.S. Provisional Patent Application No. 61/940,364, filed Feb. 14, 2014, entitled "Activity Identification Using An Optical Heart Rate Monitor," the entirety of which is incorporated herein by reference.

TECHNICAL FIELD

The present invention relates generally to electronic devices, and more particularly to wearable electronic devices. Still more particularly, the present invention relates to determining a physical activity based on a signal received from at least one optical heart rate monitor.

BACKGROUND

Portable electronic devices can be used for performing a wide variety of tasks, and in some situations the electronic device can be worn on the body of a user. For example, a portable electronic device can be worn by a user on his or her wrist, arm, ankle, or leg. One example of such an electronic device is a wrist-worn activity monitor. The activity monitor can include a heart rate monitor, a position sensor (e.g., gyroscope), and/or a motion sensor (e.g., accelerometer). The activity monitor can determine the type of physical activity based on the signals received from the heart rate monitor and the sensor(s).

Some activities, however, involve little or no limb motion during the performance of the physical activity. For example, a user's arms can remain substantially still when the user is bicycling, walking or running while pushing a stroller, exercising on an elliptical trainer or stair machine while holding the handles or side railings, and performing low-impact activities such as push-ups, squats, or sit-ups. In these situations, it can be difficult, if not impossible, for a wrist-worn activity monitor to determine the type of physical activity the user is performing. The wrist-worn activity monitor may be unable to provide information to the user about the user's physical condition or his or her performance during the physical activity. For example, the wrist-worn activity monitor may not be able to present the user with the number of steps taken by the user or the number of calories expended during the physical activity.

SUMMARY

A signal produced by an optical heart rate monitor (OHRM) can include motion artifacts or noise that are introduced into the signal during physical activity. For example, motion of the body part wearing the OHRM, motion between the OHRM and the skin, and variations in blood flow caused by body movement (e.g., a physical activity of the user) can produce motion artifacts or noise in the signal produced by the OHRM. Embodiments described herein determine the type of physical activity performed by a user by analyzing the OHRM signal that includes one or more motion artifacts.

In one aspect, an electronic device can include a processing device and one or more OHRMs operatively connected to the processing device. The processing device may be adapted to receive an OHRM signal from at least one OHRM when the user performs a physical activity. The OHRM signal includes one or more motion artifacts that are produced by the physical activity, and the processing device can be adapted to analyze the OHRM signal to determine the physical activity of the user.

In another aspect, a method for determining a physical activity of a user wearing an electronic device that includes an OHRM can include receiving an OHRM signal from the OHRM and analyzing the OHRM signal to determine the physical activity of the user. The OHRM signal includes one or more motion artifacts that are produced while the user performs the physical activity.

In another aspect, a system can include an OHRM, one or more motion and/or position sensors, and a processing device operatively connected to the OHRM and the motion and/or position sensor(s). The processing device is adapted to receive an OHRM signal from the OHRM. The OHRM signal includes one or more motion artifacts that are produced by the physical activity of the user. The processing device can also be adapted to receive a sensor signal from at least one motion and/or position sensor. The processing device analyzes the OHRM signal and the sensor signal to determine a physical activity performed by the user. Additionally or alternatively, information regarding the activity can be provided to the user. For example, data such as a heart rate, the number of steps taken, cadence information, the intensity of the activity, calorie consumption, and/or the user's speed can be provided to the user.

In yet another aspect, an electronic device includes an OHRM. The electronic device can be calibrated to determine a physical activity of a user by receiving an OHRM signal that includes one or more motion artifacts when a user performs a particular physical activity, receiving an activity identifier, and associating the activity identifier to the OHRM signal. Subsequent OHRM signals can then be correlated to an activity based on the associated activity identifier, and the identified activity may be displayed or provided to the user.

BRIEF DESCRIPTION OF THE DRAWINGS

Embodiments of the invention are better understood with reference to the following drawings. The elements of the drawings are not necessarily to scale relative to each other. Identical reference numerals have been used, where possible, to designate identical features that are common to the figures

DETAILED DESCRIPTION

Embodiments described herein provide a wearable electronic device that includes one or more optical heart rate monitors (OHRM). A signal received from at least one OHRM can include one or more motion artifacts or noise that is generated by movement of the user. Motion by the body part wearing the OHRM, motion between the OHRM and the skin, and variations in blood flow caused by body movement are example functions that can produce motion artifacts or noise in the signal output by an OHRM.

Embodiments described herein determine a physical activity of a user by analyzing an OHRM signal received from one or more OHRMs. The OHRM signal includes one or more motion artifacts that is produced by a physical activity of the user. One or more characteristics of the OHRM signal may be analyzed to determine the physical activity. For example, peak amplitudes, changes in amplitude, the distances between the peak amplitudes, time variations between peak amplitudes, the shape of the OHRM signal, and/or the frequency or frequency variations of the signal are characteristics of the OHRM signal that can be analyzed to identify the physical activity of the user.

In some embodiments, a signal produced by other types of sensors can be included in the analysis to determine the physical activity. As one example, a sensor signal from one or more motion and/or position sensors can be received and analyzed when determining a physical activity of the user. For example, when a user is mowing the lawn, a signal from an OHRM will include motion artifacts produced by the walking and/or pushing of the lawn mower. The OHRM signal can be analyzed to determine the user is mowing the lawn. Additionally, a signal from a gyroscope can detect turning position changes that indicate the user is mowing. Velocity determined from a signal received from a global positioning sensor can be consistent with the user's lawn mowing activity.

Figure 1:
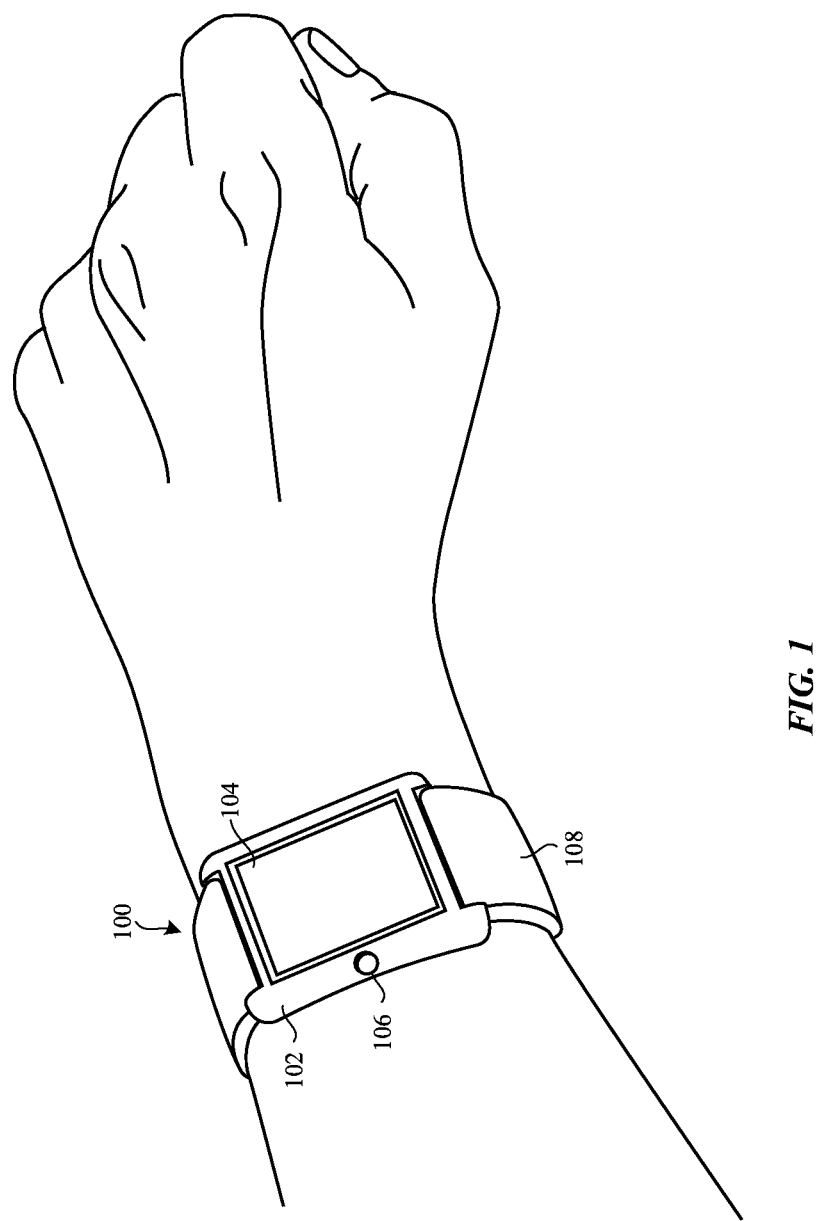
FIG. 1 is a perspective view of one example of a wearable electronic device that includes one or more optical heart rate monitors.

Referring now to FIG. 1, there is shown a perspective view of one example of a wearable electronic device that can include one or more optical heart rate monitors. Embodiments described herein include an electronic device 100 that is worn on a wrist of a user. But other embodiments can implement the electronic device differently, such as, for example, as a smart telephone, a gaming device, a digital music player, headphones or ear buds, a device that provides time, a health assistant, a fitness monitor, a medical device, and any other wearable electronic device. Additionally, the electronic device can be worn on any limb or other suitable body part (e.g., the head).

The wearable electronic device 100 includes an enclosure 102 at least partially surrounding a display 104 and one or more buttons 106 or input devices. The enclosure 102 can form an outer surface or partial outer surface and protective case for the internal components of the electronic device 100, and may at least partially surround the display 104. The enclosure 102 can be formed of one or more components operably connected together, such as a front piece and a back piece. Alternatively, the enclosure 102 can be formed of a single piece operably connected to the display 104.

The display 104 can be implemented with any suitable technology, including, but not limited to, a multi-touch sensing touchscreen that uses liquid crystal display (LCD) technology, light emitting diode (LED) technology, organic light-emitting display (OLED) technology, organic electroluminescence (OEL) technology, or another type of display technology. At least one button 106 can take the form of a home button, which may be a mechanical button, a soft button (e.g., a button that does not physically move but still accepts inputs), an icon or image on a display or on an input region, and so on. Further, in some embodiments, the button or buttons 106 can be integrated as part of a cover glass of the electronic device.

The wearable electronic device 100 can be permanently or removably attached to a band 108. The band 108 can be made of any suitable material, including, but not limited to, leather, rubber or silicon, fabric, and ceramic. In the illustrated embodiment, the band is a wristband that wraps around the user's wrist. The wristband can include an attachment mechanism (not shown) to secure the band to the user's wrist. Example attachment mechanisms include, but are not limited to, a bracelet clasp, Velcro, and magnetic connectors. In other embodiments, the band can be elastic or stretchy such that it fits over the hand of the user and does not include an attachment mechanism.

Figure 2:
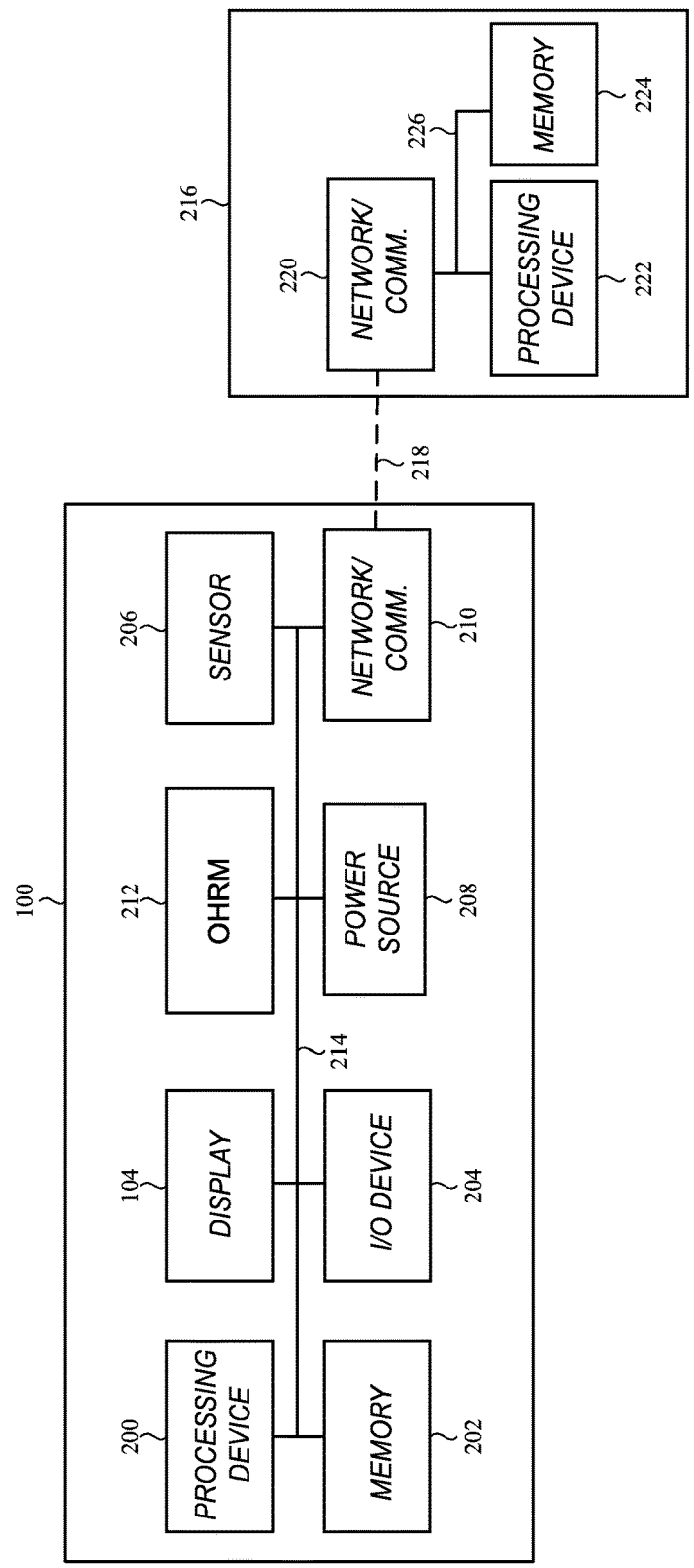
FIG. 2 is an illustrative block diagram of the wearable electronic device 100 shown in FIG. 1.

FIG. 2 is an illustrative block diagram of the wearable electronic device 100 shown in FIG. 1. The electronic device 100 can include the display 104, one or more processing devices 200, memory 202, one or more input/output (I/O) devices 204, one or more sensors 206, a power source 208, a network communications interface 210, and one or more optical heart rate monitors (OHRM) 212. The display 104 may provide an image or video output for the electronic device 100. The display may also provide an input surface for one or more input devices, such as, for example, a touch sensing device and/or a fingerprint sensor. The display 104 may be substantially any size and may be positioned substantially anywhere on the electronic device 100.

The processing device 200 can control some or all of the operations of the electronic device 100. The processing device 200 can communicate, either directly or indirectly, with substantially all of the components of the electronic device 100. For example, a system bus or signal line 214 or other communication mechanisms can provide communication between the processing device(s) 200, the memory 202, the I/O device(s) 204, the sensor(s) 206, the power source 208, the network communications interface 210, and/or the OHRM(s) 212. The one or more processing devices 200 can be implemented as any electronic device capable of processing, receiving, or transmitting data or instructions. For example, the processing device(s) 200 can each be a microprocessor, a central processing unit (CPU), an application-specific integrated circuit (ASIC), a digital signal processor (DSP), or combinations of such devices. As described herein, the term "processing device" is meant to encompass a single processor or processing unit, multiple processors, multiple processing units, or other suitably configured computing element or elements.

The memory 202 can store electronic data that can be used by the electronic device 100. For example, a memory can store electrical data or content such as, for example, audio and video files, documents and applications, device settings and user preferences, timing signals, signals received from the one or more OHRMs and sensors, calibration signals, data structures or databases, and so on. The memory 202 can be configured as any type of memory. By way of example only, the memory can be implemented as random access memory, read-only memory, Flash memory, removable memory, or other types of storage elements, or combinations of such devices.

The one or more I/O devices 204 can transmit and/or receive data to and from a user or another electronic device. One example of an I/O device is button 106 in FIG. 1. The I/O device(s) 204 can include a display, a touch sensing input surface such as a trackpad, one or more buttons, one or more microphones or speakers, one or more ports such as a microphone port, and/or a keyboard.

The electronic device 100 may also include one or more sensors 206 positioned substantially anywhere on the electronic device 100. The sensor or sensors 206 may be configured to sense substantially any type of characteristic, such as but not limited to, images, pressure or force, position, motion, speed, light, touch, heat, biometric data, and so on. For example, the sensor(s) 206 may be an image sensor, a gyroscope, an accelerometer, a global positioning sensor, a heat sensor, a light or optical sensor, a pressure transducer, a magnetometer, a health monitoring sensor, and so on.

The power source 208 can be implemented with any device capable of providing energy to the electronic device 100. For example, the power source 208 can be one or more batteries or rechargeable batteries, or a connection cable that connects the remote control device to another power source such as a wall outlet. Additionally or alternatively, the power source 208 can include a wireless energy transfer device, such as an inductive energy receiver device.

The network communication interface 210 can facilitate transmission of data to or from other electronic devices. For example, a network communication interface can transmit electronic signals via a wireless and/or wired network connection. Examples of wireless and wired network connections include, but are not limited to, cellular, Wi-Fi, Bluetooth, IR, and Ethernet.

The one or more OHRMs 212 can each measure one or more physiological functions of the user wearing the wearable electronic device 100. Each OHRM can be implemented as any suitable optical heart rate monitor. For example, in one embodiment, at least one OHRM is a reflective or transmissive photoplethysmograph (PPG) sensor. Illustrative measurements that a PPG sensor can measure include heart rate, the relative blood flow through a body part of a user, heart rate variability, and blood volume pulse. As will be described in more detail later, an OHRM signal or signals that includes one or more motion artifacts produced by a physical activity of a user is received from at least one OHRM and analyzed to identify and/or classify the physical activity of the user.

In some embodiments, the electronic device 100 can communicate with an external electronic device 216 using connection 218. Connection 218 can be a wired or wireless connection. As one example, the connection can be a cellular, Wi-Fi, or Bluetooth connection. Alternatively, a physical connector cable can connect the wearable electronic device to the external electronic device. The external electronic device 216 can be any type of electronic device, such as a computing device. Example external electronic devices include, but are not limited to, a computer such as a laptop, a tablet computing device, a smart telephone, or another wearable electronic device.

The external electronic device can include a network communication interface 220 operably connected to a processing device 222 and a memory 224. The processing device 222 can control some or all of the operations of the external electronic device 216 through bus 226. Additionally or alternatively, the processing device 222 can control some or all of the operations of the wearable electronic device 100.

It should be noted that FIGS. 1 and 2 are illustrative only. In other examples, an electronic device may include fewer or more components than those shown in FIGS. 1 and 2. Additionally or alternatively, the wearable electronic device can be in communication with other external devices. For example, a wearable electronic device may be operatively connected to, or in communication with a separate display.

As another example, a wearable electronic device can access one or more signals or data that is stored in a memory separate from the wearable electronic device.

Additionally or alternatively, in some embodiments one or more components shown in the electronic device 100 can instead be included in the external electronic device 216. For example, one or more sensors can be included in an external electronic device and the signal produced by the one or more sensors can be analyzed to determine a physical activity of the user. As one example, a user can wear the electronic device and carry a smart telephone at the same time. The wearable electronic device can be wirelessly paired to the smart telephone. A signal obtained from a global positioning sensor, a gyroscope, and/or an accelerometer in the smart telephone can be analyzed with an OHRM signal received from an OHRM in the electronic device to determine a physical activity of the user.

Figure 3:
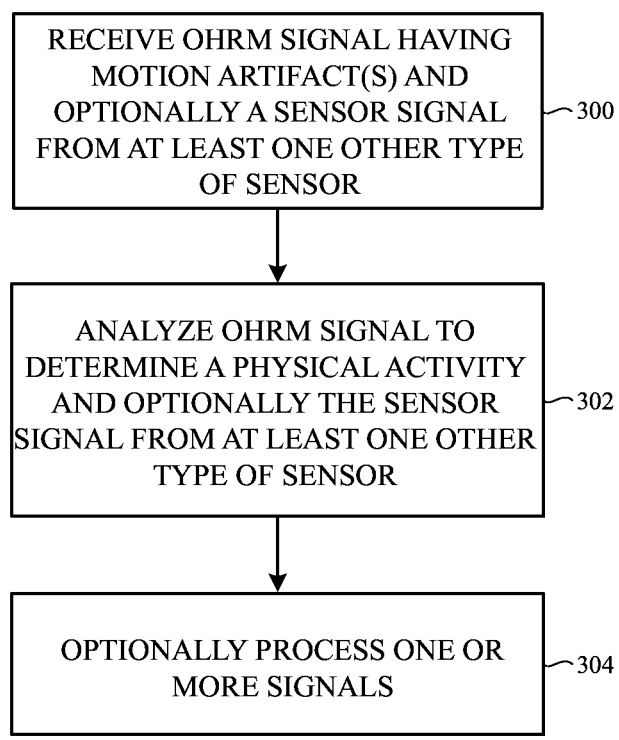
FIG. 3 is a flowchart of a method for detecting a physical activity of a user wearing an electronic device that includes one or more optical heart rate monitors.

Referring now to FIG. 3, there is shown a flowchart of a method for detecting a physical activity of a user wearing an electronic device that includes one or more OHRMs. Initially, a signal that includes motion artifacts is received from at least one OHRM at block 300. For example, movement of the body part wearing the OHRM, motion between the OHRM and the skin, and variations in blood flow caused by body movement can produce motion artifacts in the signal produced by the OHRM.

Optionally, a signal can also be received from other types of sensors at block 300. In one embodiment, a sensor signal can be received from a motion sensor and/or a position sensor. Examples of motion and position sensors include, but are not limited to, a gyroscope, an accelerometer, a global positioning sensor, a rotation vector sensor, a proximity sensor, and/or a magnetometer.

Next, as shown in block 302, the OHRM signal is analyzed to determine a physical activity being performed by the user. For example, the OHRM signal can be analyzed by the processing device 200 and/or the processing device 222 shown in FIG. 2. The analysis can identify a physical activity of the user. One or more characteristics of the OHRM signal having one or more motion artifacts may be analyzed to identify the physical activity of the user. For example, peak amplitudes, changes in amplitude, the distances between the peak amplitudes, time variations between peak amplitudes, the shape of the OHRM signal, and/or the frequency of the signal are characteristics of the OHRM signal that can be analyzed at block 302.

Optionally, a signal received from one or more other sensors can be analyzed with the OHRM signal at block 302 to determine the physical activity of the user. For example, when a user is bicycling, a signal from an OHRM will include motion artifacts produced by body position changes occurring with each leg thrust. The OHRM signal can be analyzed to determine the user is bicycling. Additionally, a signal from a gyroscope can detect turning and changes in hand position that indicate the user is bicycling. The velocity determined from a signal received from a global positioning sensor can be consistent with the activity of bicycling. And if impacts or high frequency vibrations are detected by an accelerometer, it may be possible to classify the bicycling as mountain biking instead of bicycling on a road. Thus, one or more signals received from other types of sensors, such as motion and position sensors, can be used to determine the type of physical activity and/or to further classify the type of activity.

Next, as shown in block 304, one or more of the signals can be processed to provide the user with additional information regarding the physical activity and/or his or her performance. The one or more signals may include the OHRM signal (with or without motion artifacts). Additionally or alternatively, the one or more signals may include a signal from another type of sensor. As one example, the one or more signals can be processed to provide the user with information regarding their heart rate, the number of steps taken, cadence information, the intensity of the activity, calorie consumption, and/or the user's speed. The information can be provided in real time and/or provided after the user has completed the physical activity. In one embodiment, the additional information can be displayed to the user (e.g., on display 104 in FIG. 1).

Figure 4:
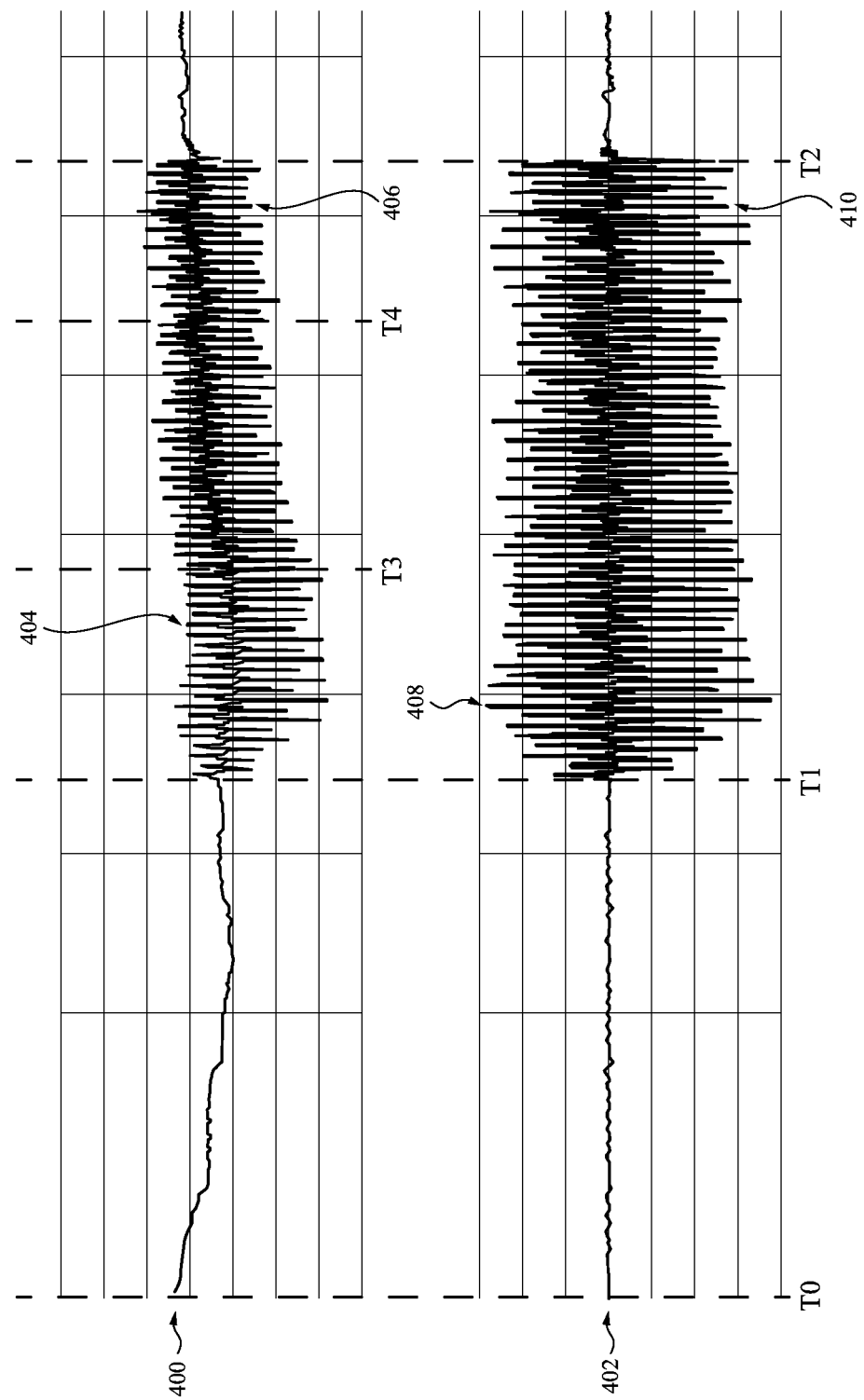
FIG. 4 depicts a first example of a photoplethysmograph signal with motion artifacts and a filtered photoplethysmograph signal.
Figure 5:
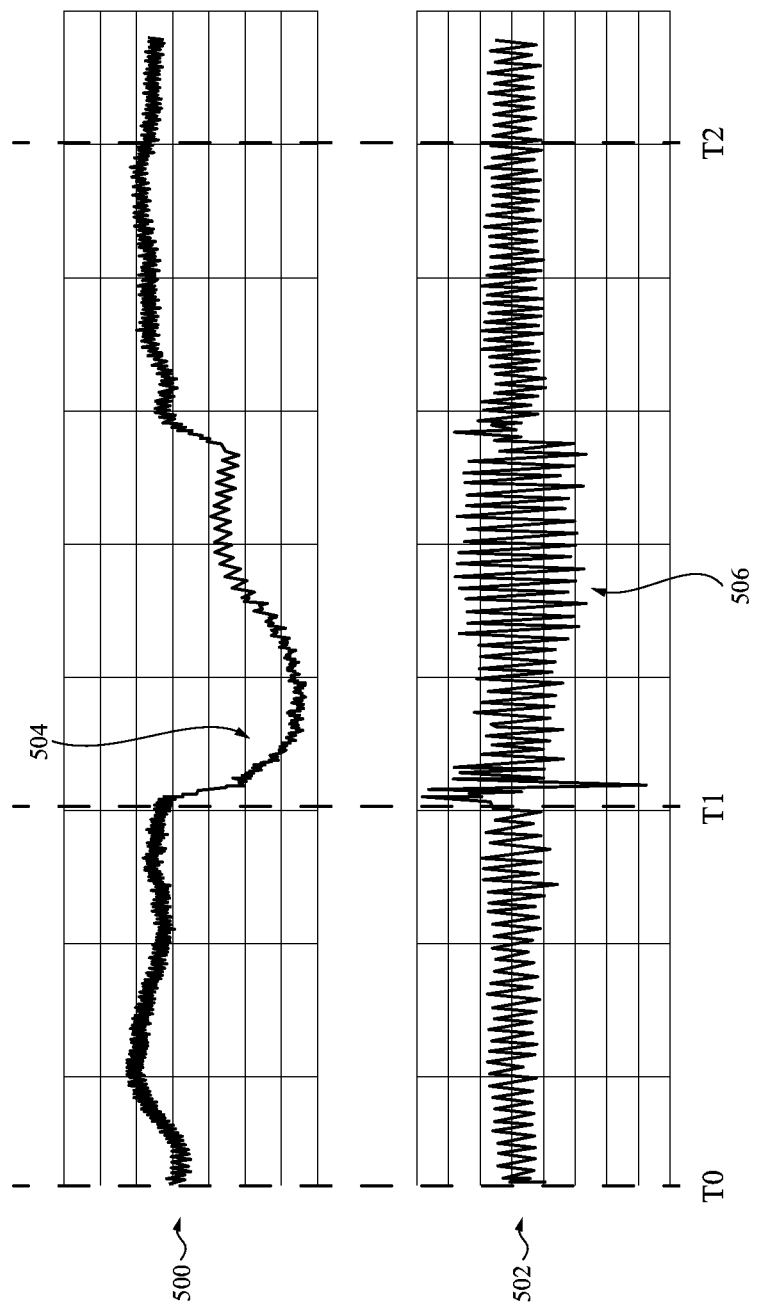
FIG. 5 illustrates a second example of a photoplethysmograph signal with motion artifacts and a filtered photoplethysmograph signal.

Two examples of a PPG signal that includes motion artifacts and a filtered PPG signal for different activities are shown in FIGS. 4 and 5. FIG. 4 illustrates a PPG signal 400 that includes motion artifacts for a user wearing the electronic device 100 shown in FIG. 1 while standing and walking without any arm movement. In the illustrated embodiment, the filtered PPG signal 402 represents the heartbeats of the user. Between time T0 and T1 the user is standing still. Consequently, both the PPG signal 400 and the filtered PPG signal 402 are substantially flat during that time period.

The user is walking in place without any substantial arm movement between the time period T1 and T2. After time T1, the PPG signal 400 includes appreciable positive and negative amplitude peaks 404, 406. Similarly, the filtered PPG signal 402 includes appreciable positive and negative amplitude peaks 408, 410. Each walking step can cause a peak amplitude in the filtered PPG signal 402 that is larger than in the PPG signal 400. At time T2, the user stops walking and begins standing still again and the PPG signal 400 and the filtered PPG signal 402 are substantially flat.

One or more characteristics of the PPG signal 400 can be analyzed to determine if the user is standing or walking. In some embodiments, the peak-to-peak distances and/or the frequencies of the peak amplitudes in the PPG signal may correlate to a physical activity. Additionally or alternatively, the shape of the PPG signal over a given time period can be analyzed to determine the type of physical activity the user is performing (i.e., walking in this illustrated embodiment). The given time period can be any period of time (or multiple periods of time) that occur during the PPG signal. For example, the given time period can be the period between time T1 and time T2, or the given time period can be one or more subset time periods between time T1 and time T2. As one example, the period between time T3 and time T4 can be analyzed to determine the physical activity of the user. Additionally or alternatively, the period between time T0 and time T4 can be analyzed.

In some embodiments, the values of the peak amplitudes and/or the distances between positive peak amplitudes and negative peak amplitudes over a given time period can be considered when determining the physical activity of the user. Additionally or alternatively, characteristics of the OHRM signal not described herein can be analyzed to determine the physical activity performed by the user.

FIG. 5 depicts a second example of a PPG signal 500 that includes motion artifacts and a filtered PPG signal 502 for a user wearing the electronic device shown in FIG. 1 while standing and squatting. Once again, the filtered PPG signal 502 represents the heartbeats of the user. The user is standing between time T0 and time T1, squatting between time T1 and time T2, and standing again after time T2. Squatting can cause a reduction in intensity 504 in the PPG signal and the heart rate can increase 506 when the user is in the squat position. As described earlier, one or more characteristics of the PPG signal can be analyzed to determine that the user is standing and/or squatting.

The OHRM signal and motion artifacts shown in FIG. 4 differs from the OHRM signal and motion artifacts in FIG. 5. Thus, physical activities can have distinct OHRM signals and motion artifacts, allowing an OHRM signal to be used to identify a specific physical activity of a user. In some embodiments, a user may calibrate a wearable electronic device by storing OHRM signals for a variety of different activities the user wants the electronic device to be able to identify.

Figure 6:
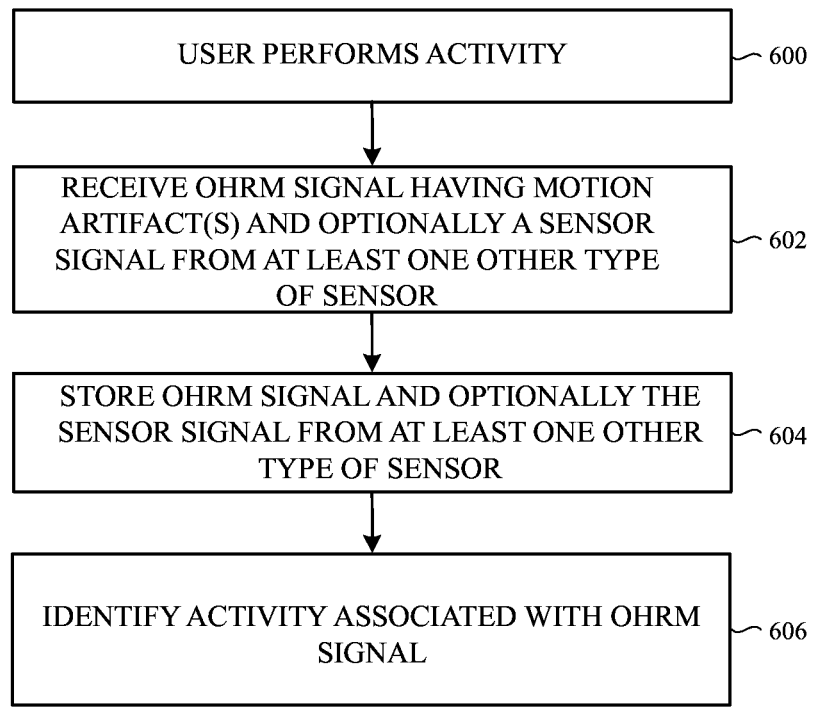
FIG. 6 is a flowchart of a method for calibrating a wearable electronic device to determine one or more activities of a user.

Referring now to FIG. 6, there is shown a flowchart of a method for calibrating a wearable electronic device to determine one or more activities of a user. Initially, the user performs the physical activity he or she wants an electronic device to be able to detect using an OHRM signal (block 600). An OHRM signal that is based on the type of physical activity that is being performed is then received at block 602. The OHRM signal includes one or more motion artifacts that is produced by the physical activity of the user. Optionally, a sensor signal from one or more other types of sensors (e.g., motion and/or position sensors) can also be received at block 602. For example, a signal from a gyroscope and/or an accelerometer can be received at block 602.

The OHRM signal having one or more motion artifacts and optionally a signal from one or more other sensors can be stored in memory. As one example, the OHRM signal can be stored in memory 202 or memory 224 shown in FIG. 2. Other embodiments can store data and/or characteristics of the OHRM signal and/or motion artifacts rather than the signal itself at block 604. Likewise, a signal and/or data and/or characteristics of the sensor signal that is received from one or more other sensors can be stored in the memory at block 604.

Next, as shown in block 606, the physical activity associated with the OHRM signal is identified and stored. An activity identifier can be received and associated with the OHRM signal. In one embodiment, the user can input an activity identifier using an input device included in the wearable electronic device. As one example, the user can input an activity identifier using a keyboard displayed on a touchscreen. In another embodiment, the user can speak the activity identifier and a voice recognition function can input the activity identification. In other embodiments, the activity identifier can be received from an external electronic device.

Subsequent OHRM signals that include one or more motion artifacts can then be correlated to an activity based on the associated activity identifier, and the identified activity may be displayed or provided to the user.

The method shown in FIG. 6 can be performed for each physical activity the user wants identified using an OHRM signal that includes motion artifacts. Other embodiments can perform the method differently. Some blocks can be omitted, new blocks added, and/or some of the blocks can be performed in a different order. For example, in some embodiments, an OHRM signal associated with a particular physical activity that is stored in memory can be updated or replaced with a newly captured OHRM signal associated with the same physical activity. A stored OHRM signal can be updated or replaced periodically, at select times, or each time the user performs the activity. In embodiments that store data and/or characteristics of the OHRM signal, the data and/or characteristics can be updated or replaced periodically, at select times, or each time the user performs the physical activity. As one example, a running average of a given OHRM signal can be maintained by updating the current OHRM signal for a particular activity with newly received OHRM signals that are determined to represent the same activity. As described previously, the OHRM signal or signals include one or more motion artifacts that is produced by the physical activity of the user.

Various embodiments have been described in detail with particular reference to certain features thereof, but it will be understood that variations and modifications can be effected within the spirit and scope of the disclosure. And even though specific embodiments have been described herein, it should be noted that the application is not limited to these embodiments. In particular, any features described with respect to one embodiment may also be used in other embodiments, where compatible. Likewise, the features of the different embodiments may be exchanged, where compatible.

What is claimed is:

1. A method for determining a type of physical activity being performed by a user wearing an electronic device that includes a photoplethysmograph (PPG) sensor, the method comprising:
   receiving, by a processing device, an optical heart rate monitor (OHRM) signal from the PPG sensor;
   analyzing, by the processing device, the OHRM signal to detect one or more signal characteristics of the OHRM signal;
   analyzing, by the processing device, the one or more signal characteristics to detect repeated motion artifacts that are produced by the type of physical activity being performed by the user;
   based on the repeated motion artifacts:
      determining, by the processing device, the type of physical activity being performed by the user;
      identifying a time period in which the determined type of physical activity is being performed by the user; and
      determining, by the processing device and using the repeated motion artifacts during the identified time period, at least one of a number of steps taken by the user during the type of physical activity or a calorie consumption by the user during the type of physical activity; and
   providing, to the user, information regarding the type of physical activity and at least one of the number of steps taken by the user during the type of physical activity or the calorie consumption by the user during the type of physical activity.

2. The method as in claim 1, further comprising:
   receiving a sensor signal from at least one other type of sensor; and
   analyzing the sensor signal when determining the type of physical activity being performed by the user.

3. The method as in claim 1, wherein analyzing the OHRM signal comprises analyzing at least one amplitude peak in the OHRM signal during a given time period.

4. The method as in claim 1, wherein analyzing the OHRM signal comprises analyzing a shape of the OHRM signal during a given time period.

5. The method as in claim 1, wherein analyzing the OHRM signal comprises analyzing a frequency of the OHRM signal during a given time period.

6. The method as in claim 1, wherein the electronic device comprises a device that provides time.

7. The method as in claim 1, wherein the electronic device comprises a health assistant.

8. An electronic device wearable by a user, comprising:
   a photoplethysmograph (PPG) sensor; and
   a processing device that is operatively connected to the PPG sensor and adapted to:
      receive an optical heart rate monitor (OHRM) signal from the PPG sensor;
      analyze the OHRM signal to detect one or more signal characteristics of the OHRM signal;
      analyze the one or more signal characteristics to detect repeated motion artifacts that are produced by a type of physical activity being performed by a user;
      based on the repeated motion artifacts, determine the type of physical activity being performed by the user;
      identify a time period in which the determined type of physical activity is being performed by the user; and
      determine, using the repeated motion artifacts during the identified time period, at least one of a number of steps taken by the user during the type of physical activity or a calorie consumption by the user during the type of physical activity; and
      provide, to the user, information regarding the type of physical activity and at least one of the number of steps or the calorie consumption.

9. The electronic device as in claim 8, further comprising a memory adapted to store one or more OHRM signals that each represent a particular type of physical activity.

10. The electronic device as in claim 8, wherein the processing device analyzes the OHRM signal by analyzing at least one amplitude peak in the OHRM signal during a given time period.

11. The electronic device as in claim 8, wherein the processing device analyzes the OHRM signal by analyzing a shape of the OHRM signal during a given time period.

12. The electronic device as in claim 8, wherein the processing device analyzes the OHRM signal by analyzing a frequency of the OHRM signal during a given time period.

13. The electronic device as in claim 8, wherein the electronic device comprises a health assistant.

14. The electronic device as in claim 8, wherein the electronic device comprises a device that provides time.

15. A system, comprising:
   a photoplethysmograph (PPG) sensor;
   a motion or position sensor; and
   a processing device operatively connected to the PPG sensor and the motion or position sensor, wherein the processing device is adapted to:
      receive from the PPG sensor an OHRM signal;
      determine one or more signal characteristics of the OHRM signal;
      analyze the one or more signal characteristics to detect repeated motion artifacts that are produced by a type of physical activity being performed by a user;
      determine the type of physical activity being performed by the user based on the repeated motion artifacts;
      receive a sensor signal from the motion or position sensor;
      analyze the sensor signal to further categorize the type of physical activity being performed by the user;
      identify, based on the repeated motion artifacts, a time period in which the determined type of physical activity is being performed by the user;
      determine, using the repeated motion artifacts during the identified time period, at least one of a number of steps taken by the user during the type of physical activity or a calorie consumption by the user during the type of physical activity; and provide, to the user, information regarding the type of physical activity and at least one of the number of steps or the calorie consumption.

16. The system as in claim 15, wherein the system comprises a wearable electronic device.

17. The system as in claim 16, wherein the PPG sensor and the processing device are included in a wearable electronic device and the motion or position sensor is included in an external electronic device communicably connected to the PPG sensor.

18. A method for operating a wearable electronic device for determining a type of physical activity being performed by a user, the wearable electronic device including a photoplethysmograph (PPG) sensor, the method comprising:
   receiving, by a processing device, an optical heart rate monitor (OHRM) signal from the PPG sensor when a user performs a particular type of physical activity;
   determining first signal characteristics of the OHRM signal;
   detecting first motion artifacts that are produced by the particular type of physical activity based on the first signal characteristics;
   receiving an activity identifier from a user of the wearable electronic device;
   associating the activity identifier to the OHRM signal to associate the particular type of physical activity to the OHRM signal;
   storing, in a memory of the wearable electronic device, the activity identifier and the OHRM signal;
   determining a subsequently received a OHRM signal is associated with the particular type of physical activity, by:
      determining second signal characteristics of the subsequently received OHRM signal;
      detecting second motion artifacts based on the second signal characteristics; and
      comparing the second motion artifacts with the first motion artifacts;
   identifying, based on the second motion artifacts, a time period in which the particular type of physical activity is being performed by the user;
   determining, using the second motion artifacts during the identified time period, at least one of a number of steps taken by the user during the particular type of physical activity or a calorie consumption by the user during the particular type of physical activity; and
   providing, to the user, information regarding the type of physical activity associated with the subsequently received OHRM and at least one of the number of steps or the calorie consumption; and
   updating the stored OHRM signal with the subsequently received OHRM signal, the updating comprising maintaining a running average of the OHRM signal associated with the particular type of physical activity.

* * * * *